US00PP21667P3

(12) United States Plant Patent
Higaki

(10) Patent No.: US PP21,667 P3
(45) Date of Patent: Jan. 25, 2011

(54) *HYDRANGEA* PLANT NAMED "DOVE"

(50) Latin Name: *Hydrangea macrophylla*
Varietal Denomination: Dove

(75) Inventor: Harrison M Higaki, San Mateo, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 28 days.

(21) Appl. No.: 12/315,187

(22) Filed: Nov. 29, 2008

(65) Prior Publication Data

US 2010/0138967 P1 Jun. 3, 2010

(51) Int. Cl.
*A01H 5/00* (2006.01)

(52) U.S. Cl. ..... Plt./250

(58) Field of Classification Search ..... Plt./250
See application file for complete search history.

(56) References Cited

U.S. PATENT DOCUMENTS

PP15,912 P3 * 8/2005 Higaki ..... Plt./250
PP20,614 P2 * 12/2009 Eveleens ..... Plt./250

* cited by examiner

*Primary Examiner*—Wendy C. Haas
(74) *Attorney, Agent, or Firm*—Charles R. Cypher; James R. Cypher

(57) ABSTRACT

A new and distinct cultivar of *Hydrangea macrophylla* (Thunb.) named 'Dove ' originated as a controlled cross between the cultivars 'BuffiexLibelle96BL-2' and 'Libelle'. The cultivar 'Dove' has white R.H.S. 155 D (white group) sepals at maturity and is distinguished from other similar cultivars of which the inventor is aware by its sepal color, and its compact and sturdy growth habit. 'Dove' has large showy inflorescences, having both sepalous and non-sepalous florets.

5 Drawing Sheets

Botanical classification: *Hydrangea macrophylla* (Thunb.) 'Dove'.

Variety denomination: 'Dove'.

BACKGROUND OF THE INVENTION

This invention relates to a new and distinct cultivar of the *Saxifragaceae* family. The botanical name of the plant is *Hydrangea macrophylla* (Thunb.) 'Dove'.

The new cultivar originated as a seedling from a controlled cross between the commercial variety *Hydrangea macrophylla* (Thunb.) 'Libelle' and the commercial variety *Hydrangea macrophylla* (Thunb.) 'Buffie'. The progeny from that cross were evaluated and two of the progeny were selected for further development. One of the progeny, identified by the inventor as *Hydrangea macrophylla* (Thunb.) 'BuffiexLibelle96BL-2' was crossed back to *Hydrangea macrophylla* (Thunb.) 'Libelle'. The progeny of this cross were evaluated and the cultivar which is the subject of this application was selected: *Hydrangea macrophylla* (Thunb.) 'Dove'.

The variety 'Dove' has white sepals like the parent 'Libelle', and is typically grown under soil conditions with pH conditions that would produce pink pigmentation, if the sepals were pigmented.

The new variety was first noticed, because of its strong stems and upright growth habit. Unlike its parent 'Libelle' which it most closely resembles, the new variety's stems are strong, like its relative 'Buffie'.

The new cultivar 'Dove' has been successfully asexually reproduced under controlled environmental conditions at a nursery in Half Moon Bay, Calif. under the direction of the inventor through three genera with its distinguishing characteristics remaining stable.

'Dove' is distinguished from other lace cap varieties of *Hydrangea* of which the inventor is aware by its strong stems, upright but compact growth habit and sepal color. 'Dove' is distinguished from 'Buffie' by the form of its inflorescence. 'Dove' is a lace cap type *hydrangea* with the non-sepalous florets dominating the inflorescence, while 'Buffie' has a ball-type inflorescence with the sepalous florets dominating and hiding the non-sepalous florets. 'Dove' has stronger stems than the variety 'Libelle' from which it is derived as it does not have to be staked for commercial sale.

Asexual reproduction was first accomplished when vegetative cuttings were taken from the initially selected plant. Examination of asexually reproduced, successive generations grown in a nursery at Half Moon Bay, Calif. show that the combination of characteristics as herein disclosed for 'Dove' remains firmly fixed through three generations.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
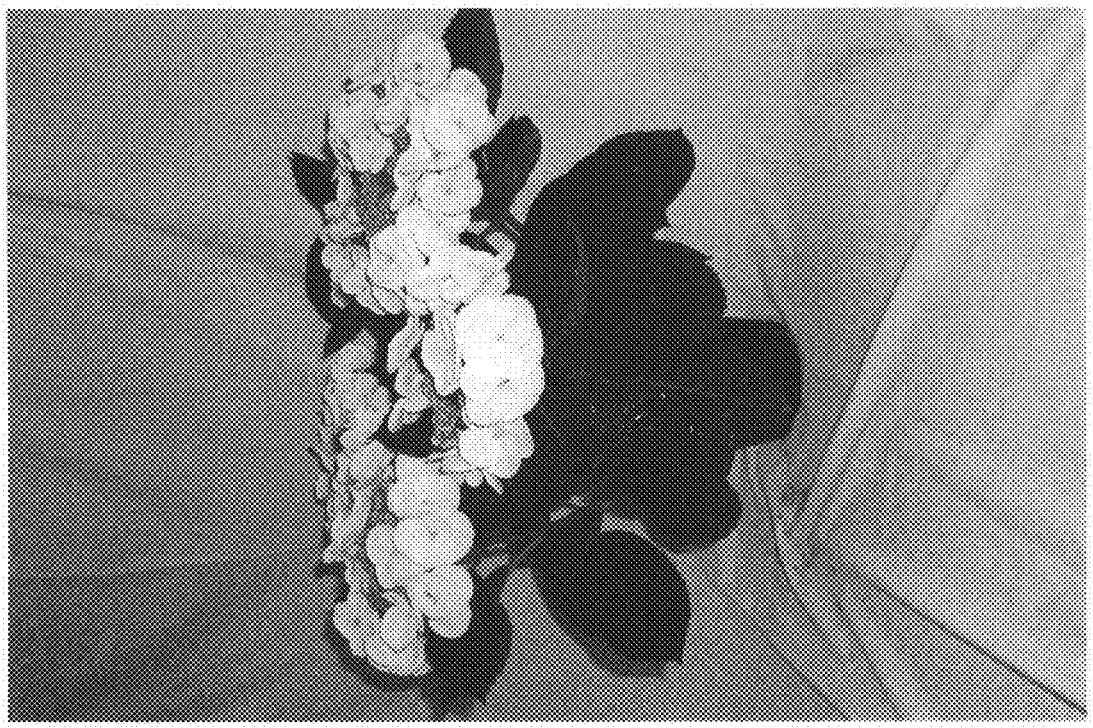
FIG. 1 is a view of the entire plant showing its form, compact growth habit, dark green foliage, inflorescence, and white sepals. The particular plant shown has multiple panicles.
Figure 2:
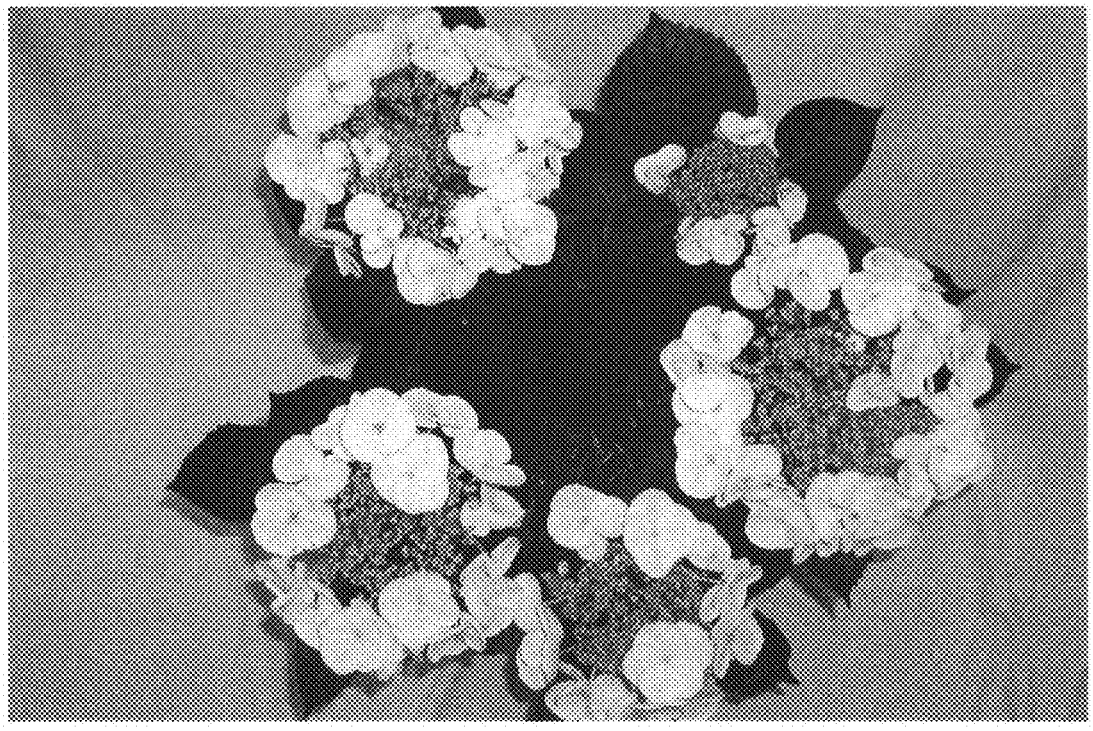
FIG. 2 is a top view of the entire plant. The particular plant shown has multiple panicles.
Figure 3:
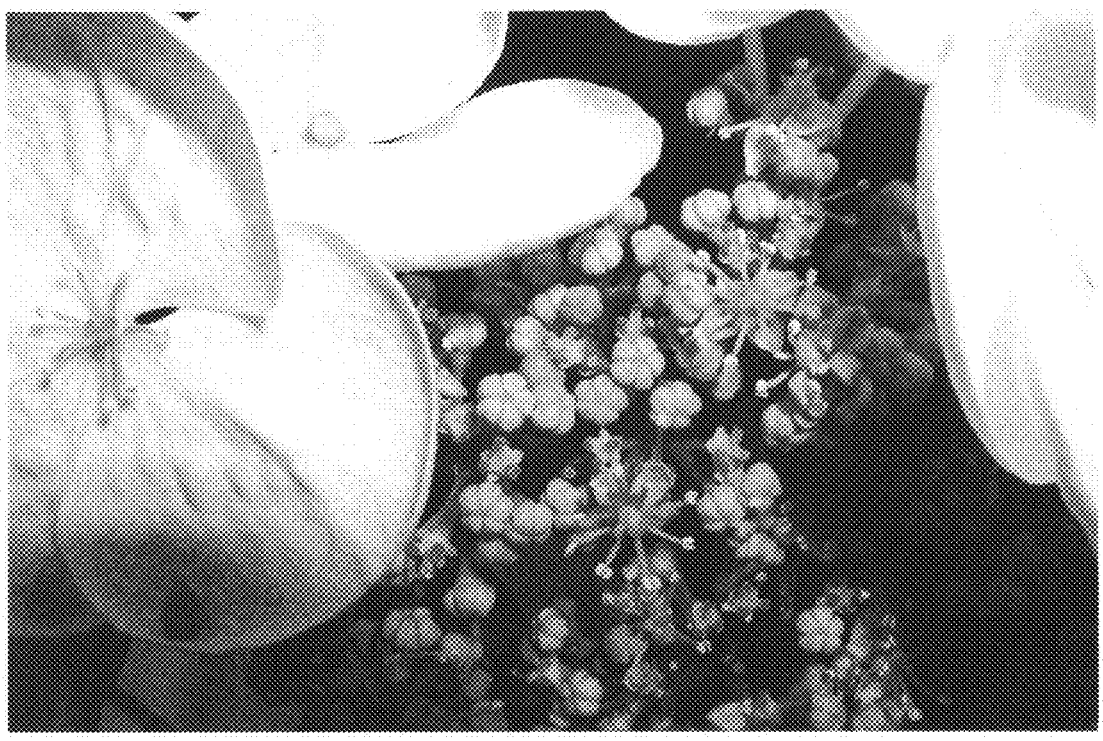
FIG. 3 is a close-up view of a panicle of the new variety, showing opened, sepalous florets.
Figure 4:
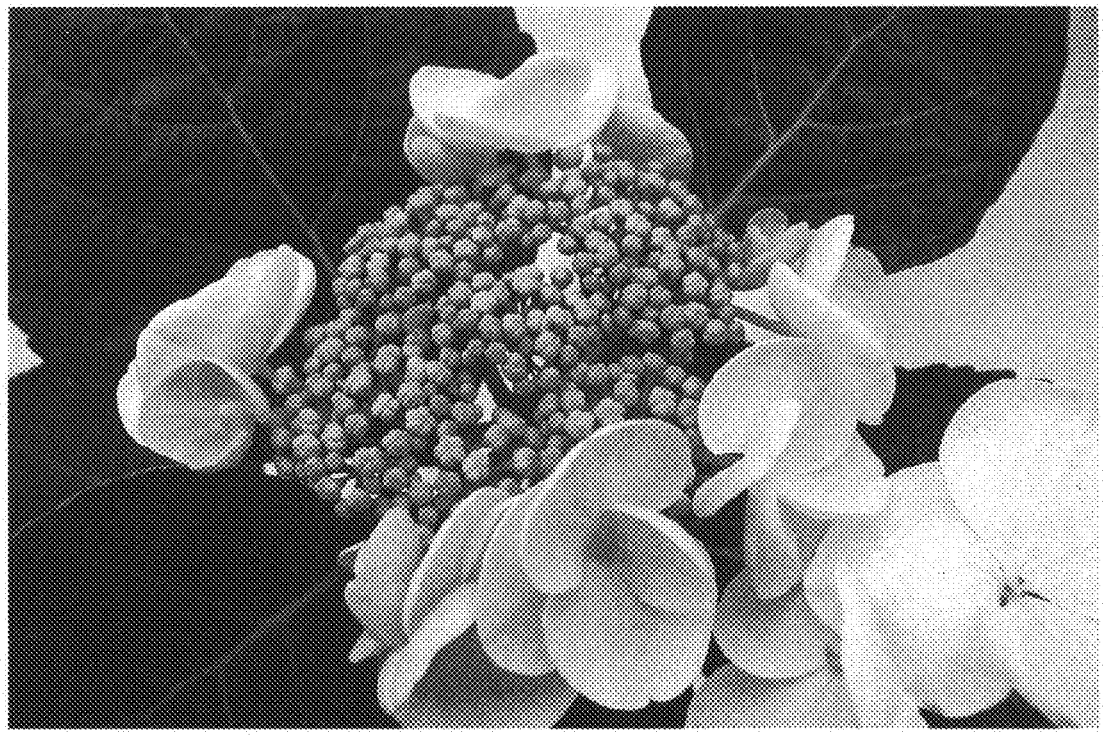
FIG. 4 is a close-up view of a panicle of the new variety. The panicle shown is still rather young. The sepalous florets are still opening.
Figure 5:
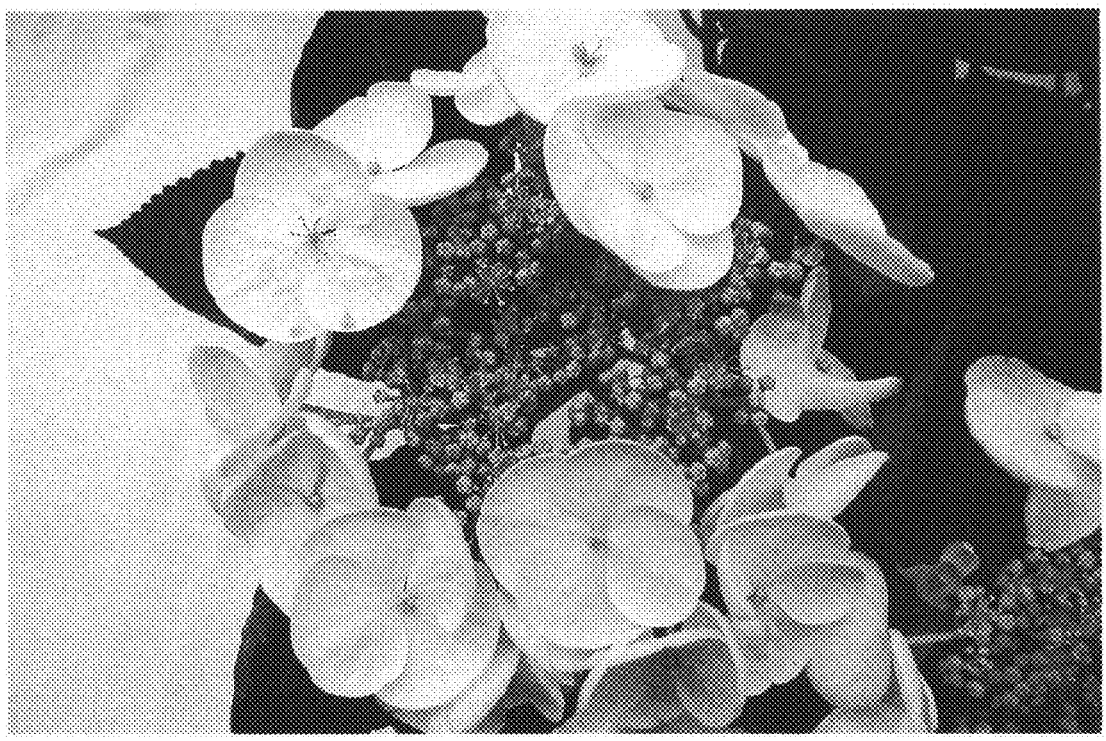
FIG. 5 is a close-up view of a panicle of the new variety.
Figure 6:
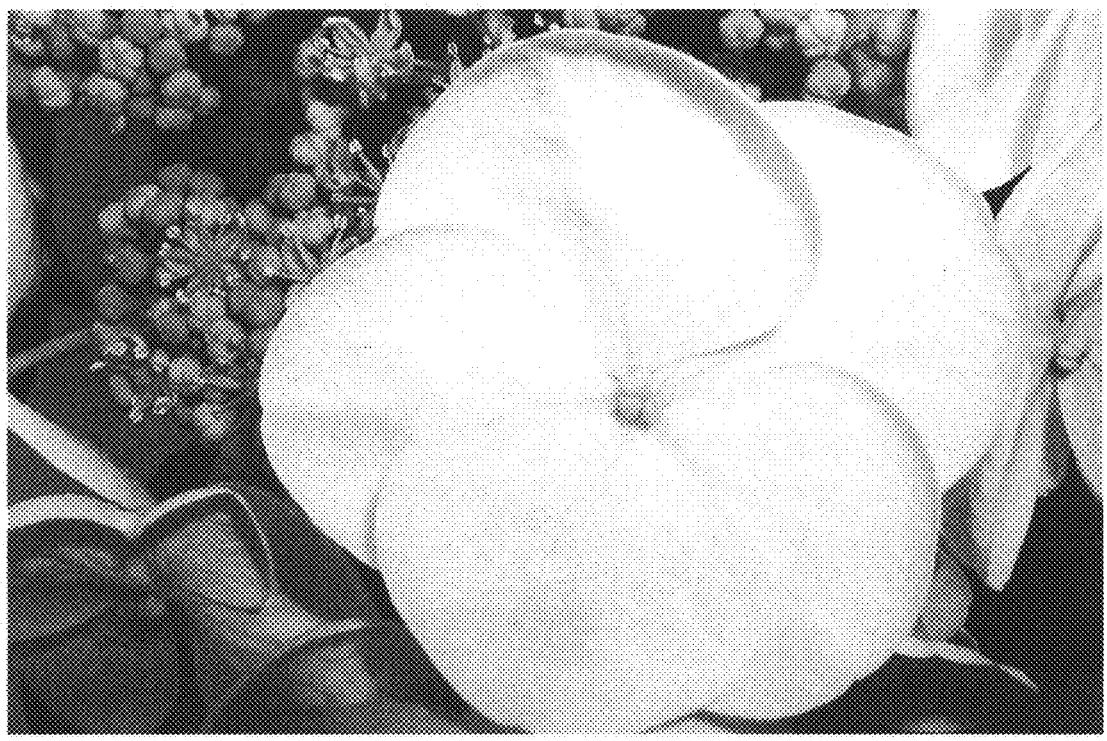
FIG. 6 is a close-up view of a mature floret of the new variety.
Figure 7:
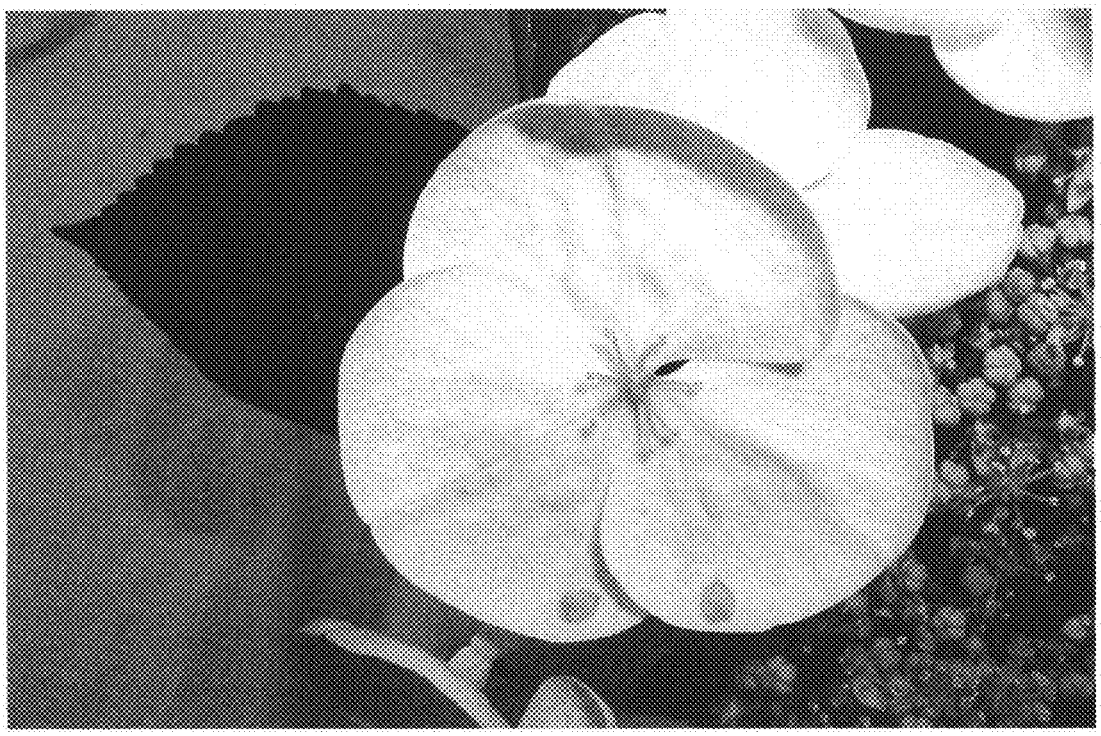
FIG. 7 is a close-up view of a mature floret of the new variety.
Figure 8:
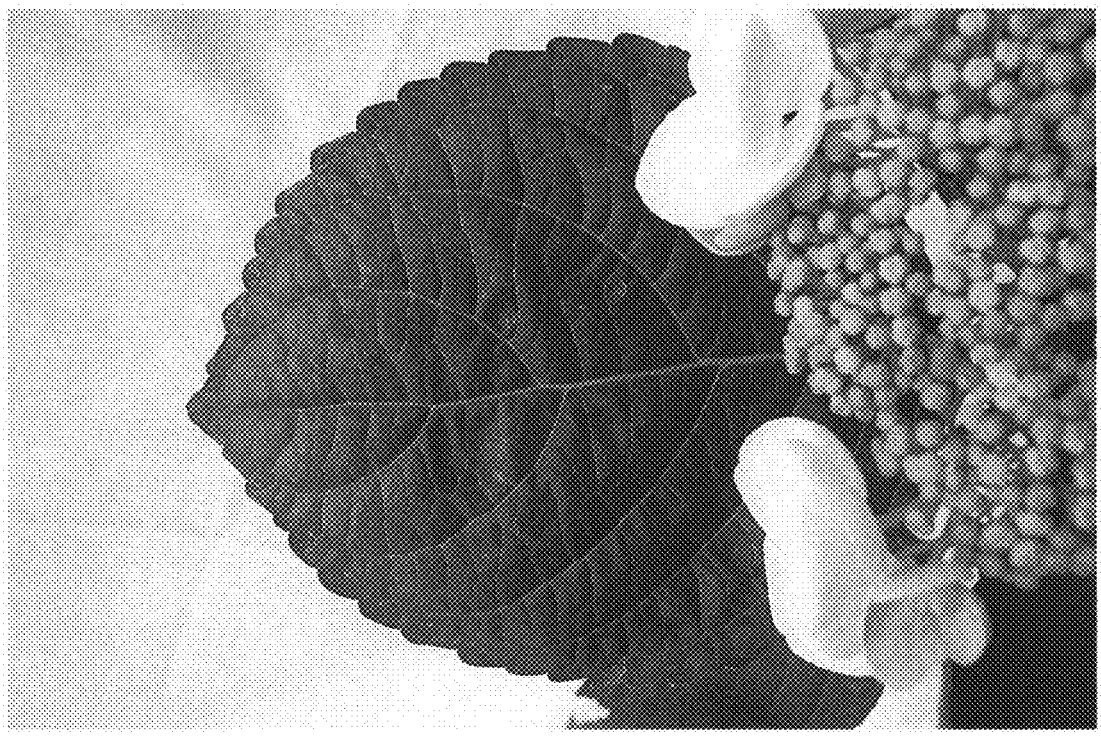
FIG. 8 is a close-up view of the adaxial surface of a mature leaf.
Figure 9:
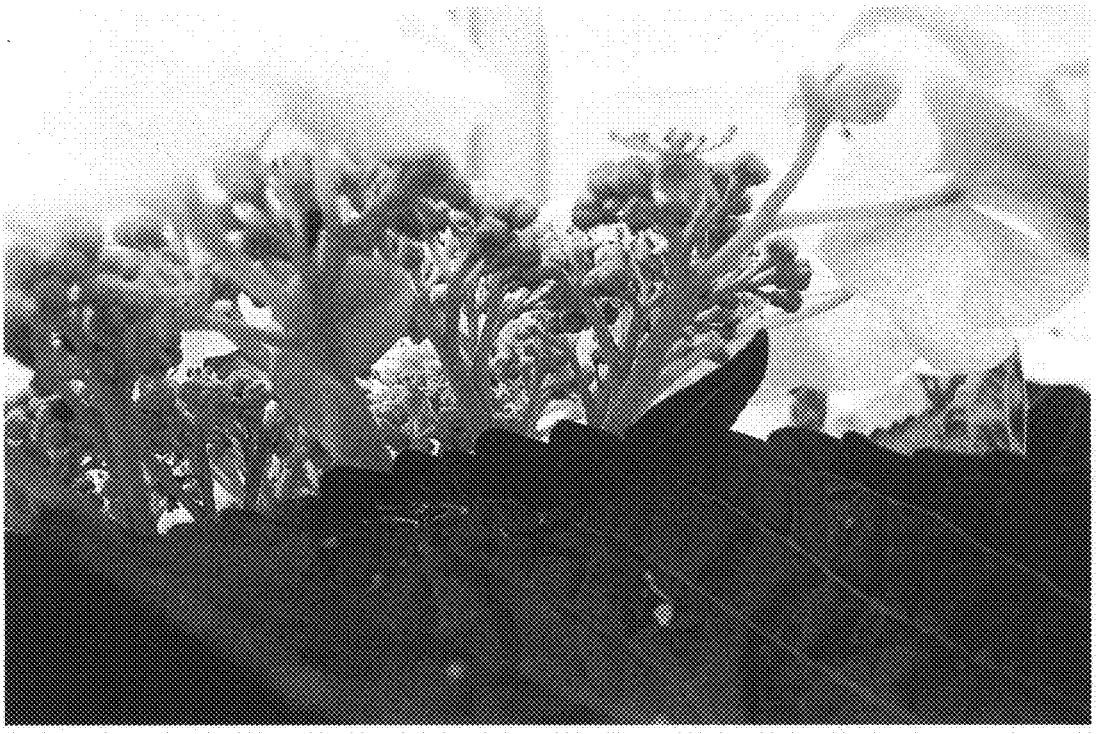
FIG. 9 is a close-up view of the underside of a panicle, showing lenticels on the stem.
Figure 10:
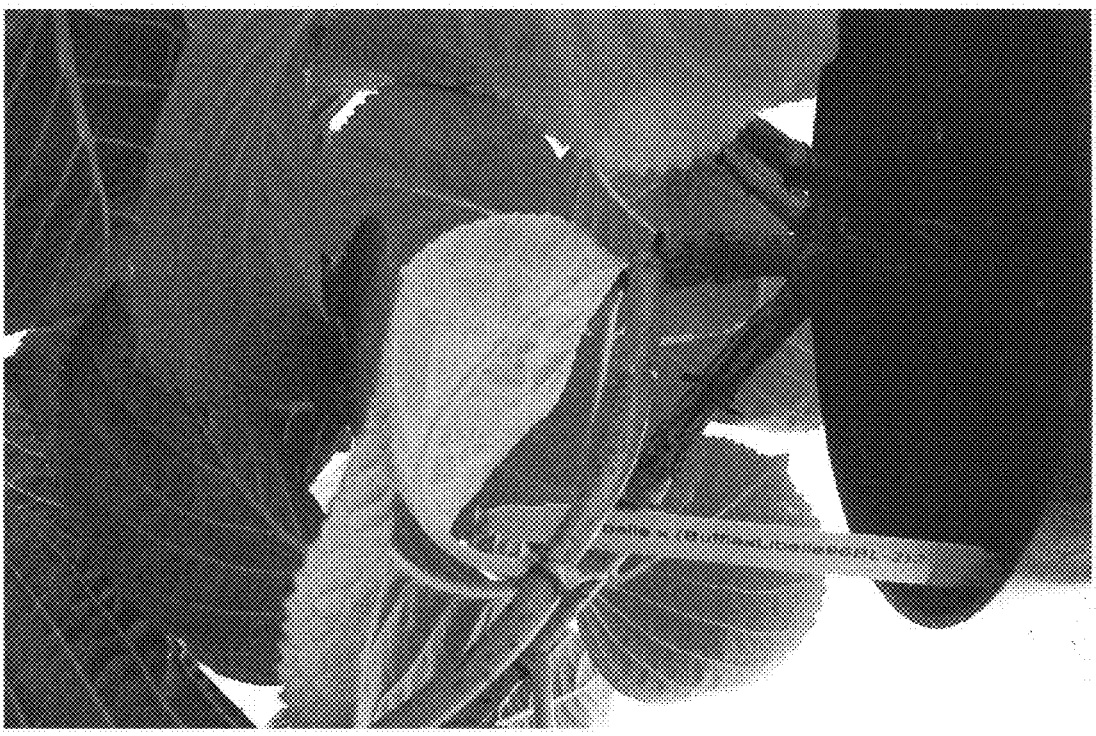
FIG. 10 is a close-up view of the base of the stem.

The plants shown in the figures started out as cuttings, taken from the stem of a grown plant. The cuttings were placed in a 6" pot with hydrangea soil that would produce pink pigmentation in *Hydrangeas* that have pigmentation in their sepals.

'Dove' has not been observed under all possible environmental conditions. The phenotype may vary significantly with variations in environment such as temperature, light intensity and day length. Color determinations were made with The Royal Horticultural Society (R.H.S.) Colour Chart.

THE PLANT

Origin: Controlled cross.

*Parents.*—*Hydrangea macrophylla* (Thunb.) 'Libelle' (unpatented) and *Hydrangea macrophylla* (Thunb.) 'BuffiexLibelle96BL-2' (unpatented).

*Botanic classification.*—*Hydrangea macrophylla* (Thunb.) Dove.

Form: Upright, compact shrub. A typical plant with a mature inflorescence that is ready for sale is approximately 14" high, has 6 inflorescences after being pinched, and has a diameter of 20" when grown in a 6" pot with appropriate soil amendments. Bottom 2.5 to 5 inches of the stems are woody.

Growth: Upright, vigorous growth habit. Inflorescence is large. The plant branches easily with shoots forming at the base of the plant. Lateral branches are similar in appearance and form to the main stems.

Stems: Lenticels are present. Stems become woody as they age. The color of typical young stems and young lateral branches is R.H.S. 146 D (yellow-green group). Woody stems are R.H.S. 199 D (grey-brown group). The lenticels are R.H.S. 182 A (greyed-red group).

Foliage: Abundant. Leaves are opposite on stem and lateral branches.

*Shape of leaf.*—Elliptic with acute base and apex. Margins are serrate.

*Texture.*—Glabrous; veins dominate on the underside of the leaf and are sunken on the leaf surface.

*Color.*—Mature leaves have an upper side that is R.H.S. 137 A (green group), and an under side that is R.H.S. 147 B (yellow-green group). The upper side of younger leaves can be a little darker at R.H.S 139 A (green group). The veins of mature leaves are R.H.S. 145 C (yellow-green group) whether viewed from the top or the bottom of the leaf. Leaves are pinnately veined. The midvein and veins branching off the midvein are large and prominent on the underside of the leaves. Large leaves are 6 inches long (not including the petiole) and 4.5 inches wide. Smaller leaves are 5 inches long and 3.5 inches wide. Petiole lengths range from 1 to 2 inches.

BUDS

Form: Globose with 4 to 5 connate petals (sometimes 3). Buds in the center of the inflorescence are non-sepalous and dominate the inflorescence. Buds have a diameter of approximately 5 mm at maturity. Very young floret buds are R.H.S. 145C (yellow-green group), turning pink as they age.

Aspect: Smooth.

Arrangement: Borne on branched panicles.

INFLORESCENCE

Form: Paniculate. Terminal. As many as 200 or more individual flowers (florets) per inflorescence. Both sepalous florets and non-sepalous florets borne on same panicle, with the sepalous florets forming a ring around the edge of the inflorescence. An inflorescence with 200 florets may have as many as 20-30 sepalous florets. Flowers do not produce a fragrance. The peduncle or panicle for the inflorescence is branched, strong and upright. The uppermost portions of the pedicels for the individual florets are predominately pink—R.H.S. 69 A (red-purple group) at maturity.

Size of inflorescence: Large. Individual inflorescence size is dependent on the number of florets. A typical inflorescence can grow as large as 9" in diameter, and 5" high.

Shape: Clusters of numerous small florets; sepalous florets are flat and overlapping one another. Sepals are persistent.

Appearance: Showy.

FLORETS

*General.*—The non-sepalous florets at the center of the inflorescence open first. Sepalous florets are perfect and complete, although petals, stamens and ovary generally fall off. Corolla: Generally there are 4 petals that are pink — R.H.S. 69 A (red-purple group).

*Stamens.*—10 stamens (some florets have 8 or 9). Pollen is yellow — R.H.S. 8D (yellow group). Plant produces abundant pollen. Filament is pink — R.H.S. 69 A (red-purple group) and approximately 4 mm long. Anther is 1 mm long and is regular and basally attached.

*Stigma.*—Generally, a three-pronged stigma on one pistil per floret. Stigma is pink — R.H.S. 69 A (red-purple group) and protrudes from the ovary approximately 1 mm.

*Ovary.*—Ovary is green — R.H.S. 145 C (yellow-green group) when young, becoming pink at the floret matures and is partially inferior.

Sepalous florets:

*General.*—Veins dominate on the underside of the sepals.

*Number of sepals.*—4 or 5 sepals per floret, usually 4, and sometimes 3.

*Aspect of sepals.*—Smooth and glaucescent.

*Shape of sepals.*—Reniform with acuminate apex. Edges often wavy when the floret is young.

*Size of sepals.*—As the florets mature, the sepals enlarge and overlap each other. Usually 1 dominant sepal, 2 smaller but equally-sized sepals, and 1 small sepal. Largest sepal at maturity is typically 27 mm long and 40 mm wide, the medium sized sepals are typically 25 mm long by 33 mm wide, and the smallest sepals are typically 25 mm long and 27 cm wide.

*Coloration of sepals.*—At maturity the sepals are white — R.H.S. 155 D (white group). Young sepals are R.H.S.145 C (yellow-green group).

Fruit: None.

I claim:

1. A new and distinct *Hydrangea macrophylla* (Thunb.) plant named 'Dove' substantially as herein shown and described.

* * * * *